(12) United States Patent
Wu et al.

(10) Patent No.: US 8,702,645 B2
(45) Date of Patent: Apr. 22, 2014

(54) IMPLANTABLE-GLUCOSE RESPONSIVE INSULIN DELIVERY DEVICE

(75) Inventors: Xiao Yu Wu, Toronto (CA); Kai Zhang, Wayne, PA (US); Huiyu Huang, North York (CA); Claudia Gordijo, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 264 days.

(21) Appl. No.: 13/101,634

(22) Filed: May 5, 2011

(65) Prior Publication Data

US 2011/0276025 A1 Nov. 10, 2011

Related U.S. Application Data

(60) Provisional application No. 61/331,690, filed on May 5, 2010.

(51) Int. Cl.
*A61M 31/00* (2006.01)

(52) U.S. Cl.
USPC .......... 604/66; 604/503; 604/890.1; 424/424; 424/426

(58) Field of Classification Search
USPC .................. 604/890.1, 66, 503; 424/424–426
See application file for complete search history.

(56) References Cited

U.S. PATENT DOCUMENTS

| 5,226,902 | A | * | 7/1993 | Bae et al. ............ 604/892.1 |
| 6,565,872 | B2 | | 5/2003 | Wu et al. |
| 6,858,403 | B2 | | 2/2005 | Han et al. |

OTHER PUBLICATIONS

Gordijo et al., "A New Bio-Inorganic Nanocomposite Membrane for Glucose-Modulated Release of Insulin," MRS Symposium Proceedings (Dec. 2009) (poster).
Gordijo et al., "Nanofunctionalized Glucose-Responsive Implantable Devise for Self-Regulated Insulin Release," MRS Functionalized Nanobiomaterials for Medical Applications, (Oct. 2010) (oral presentation).
Gordijo et al., "Closed Loop Insulin Delivery Device: Fabrication in vitro and in vivo Evaluation of Self-Regulated Insulin Release," Diabetes Technology Soc. Annual Meeting (Nov. 2009) (poster).
Gordijo et al., "Glucose-Responsive Bionorganic Nanohybrid Membrane for Self-Regulated Insulin Release," Adv. Func. Mater., 20:1-9 (2010).

\* cited by examiner

*Primary Examiner* — Kevin C Sirmons
*Assistant Examiner* — Deanna K Hall
(74) *Attorney, Agent, or Firm* — Cesari and McKenna, LLP

(57) ABSTRACT

A biocompatible insulin delivery device is provided comprising an insulin reservoir sealed with a glucose-responsive plug or membrane. The plug functions to release insulin from the reservoir in response to a hyperglycemic glucose concentration and to prevent insulin release from the reservoir in response to hypoglycemic glucose concentration. In one embodiment, the plug is made of a biocompatible polymeric matrix comprising an inorganic component, a stimulus-responsive component and a catalytic component.

17 Claims, 11 Drawing Sheets

IMPLANTABLE-GLUCOSE RESPONSIVE INSULIN DELIVERY DEVICE

FIELD OF THE INVENTION

The present invention relates generally to the field of insulin delivery, and in particular, to a glucose responsive insulin delivery device.

BACKGROUND OF THE INVENTION

Diabetes is a serious medical condition characterized by the body's inability or deficiency to metabolize glucose. This disease affects almost 250 million people worldwide and is the $4^{th}$ leading cause of death globally. The number of diabetes patients is expected to increase to at least 300 million in 2025. There are two major types of diabetes mellitus: Type 1 diabetes, caused by insufficient secretion of insulin due to the damage of pancreatic beta cells, which requires frequent administration of exogenous insulin to sustain life; and Type 2 diabetes, often caused by inadequate endogenous insulin to control glucose levels, which is currently managed through dietary modifications, exercise, medication, or through insulin injections in about 20% of the cases. In both types of diabetes, hypoglycemia frequently results from the use of insulin, owing to a very poor approximation of normal physiological insulin secretion that is tightly modulated by glucose levels. In order to maintain blood glucose levels within the normal range, diabetic patients have to administer insulin periodically prior to meals or when it is needed as indicated by self-examination of blood glucose levels. This process is painful, inaccurate, inconvenient, and cannot monitor and deliver necessary insulin at night during sleep. Therefore, research has been conducted actively in past decades to explore better ways of monitoring glucose concentration and delivering insulin continuously and automatically. Unfortunately, development of glucose-responsive insulin delivery systems has still been unsatisfactory, though a few glucose sensors have been or are being developed. In addition, linking the sensor with the insulin pump has been attempted.

Different approaches to insulin delivery have been investigated including delivery of insulin via oral, nasal, or pulmonary routes and transplantation of islet cells. Except for the latter approach, other treatment options cannot provide automatic supply of insulin when needed. Transplantation of pancreatic islet cell into patients was conducted in multicenter clinical trials of Edmonton Protocol (Canada) and showed great promise of normalizing a patient's pancreatic functions. However, because of chronic use of immunosuppressive drugs, limited sources of the cells (only sufficient islets from donors to treat 0.1% of the true need in type 1 diabetes), and the high cost of the treatment ($140K per patient), renders this approach unavailable to the majority of patients. Moreover, to date, long-term function of the transplanted islets has been difficult to accomplish with only 10% of patients maintaining insulin independence 5 years after transplantation. Even for those patients receiving islet cell transplant, interim insulin treatment is necessary to preserve the function of the islet cells at the outset.

Animals, just like humans, can acquire Type 1 or Type 2 diabetes. Canine diabetes is an endocrine disorder which is seen in pets such as cats and dogs and in big animals like horses. Diabetes in animals requires daily management and, in most cases, treatment by owners. In this case, the burden and difficulty of administering treatment and the costs associated with treatment rests on the pet/animal owners. Type I diabetes in animals occurs when there is a lack of insulin production and secretion by the pancreas. This form is identified in approximately 50 to 70% of cats diagnosed with diabetes mellitus, and requires insulin injections to control the disease. Most cats will require one or two daily injections of insulin to control blood glucose. Diabetic dogs almost always (99%) have Type I diabetes and also require one or two daily injections of insulin. The injections are given under the skin using a small needle. Dogs tend to get diabetes early in life. For instance, juvenile-onset diabetes (Type 1) may occur in dogs at less than 1 year of age. Although cats tend to get diabetes later in life, e.g. middle-aged to older, it may also occur in cats younger than 1 year of age.

Type II diabetes occurs when enough insulin is produced but something interferes with its ability to be utilized by the body. This form is identified in approximately 30% of cats with diabetes mellitus. In order to maintain blood glucose levels within the normal range, diabetic animals need to have insulin administered periodically prior to meals or when it is needed as indicated by glucose level examination. As animals cannot do this for themselves, owners have to make sure that their animals are getting the proper treatments at very specific times. The process is painful and uncomfortable for the animals, can be inaccurate and inconvenient, and is clearly a burden on a pet owner.

Numerous groups have attempted to develop closed-loop insulin delivery systems (SRIDS). The principle of SRIDS is to integrate a sensing element and a responsive release mechanism into one system. In addition to the biological approach, i.e., islet cell transplantation, electromechanical and physiochemical approaches have been investigated. In the electromechanical approach, an insulin pump infuses insulin controlled by a computer that receives signals from a glucose sensor. However, to date, no integrated closed-loop insulin pump system is available for human use. Currently available insulin pumps deliver insulin continuously and subcutaneously or intraperitoneally in the case of the external pumps. In 2006 a sensor-augmented pump, the Mini-Med Paradigm® REAL-Time System (Medtronic Diabetes, California) received FDA approval. This system consists of a CGMS Guardian RT glucose monitor and an insulin pump. Although this system can offer better control of blood glucose levels than periodic injections, it is not a closed-loop system. It provides real-time information about carbohydrate count and historical data based on which pump settings can be adjusted by users thus achieving better control of glucose levels. Integrated systems are also being investigated using microdialysis, subcutaneous or intravenous sensors, together with implanted pump or external pump.

While significant progress has been made to close the loop between glucose sensor and insulin delivery pump, this electromechanical approach is not without problems. For example, insulin pumps were recalled due to patient injuries and even deaths associated with use of the pumps. Transmission of blood sugar signals to the pump via radio frequency may interfere with cell phones or radio traffic giving problems inside airplanes. Moreover, the users still need to conduct finger pricking measurements for calibrating the sensors every 24 or 48 hours.

Physicochemical approaches to the development of SRIDS utilize physical interactions or chemical reactions that trigger changes in polymer properties allowing more or less insulin to be delivered. Similar to the principal mechanism of most glucose sensors, glucose oxidation by glucose oxidase (GOx) is used to generate pH or hydrogen peroxide signals. Polymers containing amino groups swell at lower pH in response to higher glucose levels allowing more insulin to be released either by creating larger pores or by pushing insulin solution out. The disadvantages of such an approach include slow response of the bulk hydrogels, weak mechanical strength, and possible binding of negatively charged insulin with positively charged polymers hindering insulin release. Carboxyl group-containing polymers, e.g. poly(acrylic acid), were grafted onto a porous membrane/filter and used to regulate insulin release by glucose oxidation. This method offered a faster response and higher mechanical strength than the bulk hydrogel, however, it resulted in very low enzyme immobilization and difficult control of surface grafting. Redox polymers have been applied with glucose oxidation, however, hydrogen peroxide is produced. The polymers changed from reduced form (hydrophobic) to oxidized form (hydrophilic), thus increasing the permeability of insulin through the polymer. This method suffers a very small change (<1.5-fold increase) in insulin permeability as glucose concentration was raised from zero to 5,000 mg/dL, which is unrealistically high as compared to 200-400 mg/dL, hyperglycemia levels in the body.

Competitive binding of glucose with sugar ligands and competitive binding of glucose with polymers are other physicochemical approaches. Glycosylated insulin forms a complex with lectin. As free glucose diffuses into the complex, the glycosylated insulin is replaced and released out. This binding mechanism is non-specific because other endogenous sugars can also bind with lectin, resulting in false signals. Competitive binding of free glucose with polymers is also used to induce polymer swelling or dissolving, thus increasing insulin release. This method is also problematic because other diols or sugars in the body can bind to boronic acid and concanavalin-A.

In view of the foregoing, it is evident that there is a need to develop alternative ways of treating diabetes, in both humans and animals, that allow for effective and accurate treatment.

SUMMARY OF THE INVENTION

A closed-loop implantable insulin delivery device has now been developed that functions to control insulin release continuously and automatically in vivo in response to blood glucose levels.

In one aspect of the invention, a biocompatible insulin delivery device is provided comprising an insulin reservoir sealed with a glucose-responsive plug or membrane, wherein the plug or membrane functions to release insulin from the reservoir in response to a hyperglycemic glucose concentration and to prevent insulin release from the reservoir in response to hypoglycemic glucose concentration.

In another aspect of the invention, a biocompatible glucose-responsive membrane is provided that comprises a polymeric matrix having an inorganic component and a stimuli-responsive component adapted to alter the porosity of the matrix in response to a change in glucose concentration.

In a further aspect, a method of treating diabetes is provided comprising implanting a biocompatible insulin delivery device into the mammal, wherein the device comprises an insulin reservoir sealed with a glucose-responsive plug or membrane, wherein the plug or membrane functions to release insulin from the reservoir in response to a hyperglycemic glucose concentration and to prevent insulin release from the reservoir in response to hypoglycemic glucose concentration.

These and other aspects of the present invention will become apparent from the following detailed description by reference to the figures. It should be understood, however, that the detailed description and the specific examples while indicating preferred embodiments of the invention are given by way of illustration only, since various modifications and changes within the spirit and scope of the invention will become apparent to those skilled in the art from this detailed description.

DETAILED DESCRIPTION OF THE INVENTION

A biocompatible insulin delivery device is provided comprising an insulin reservoir capped with a glucose-responsive membrane or plug. The membrane/plug functions to release insulin from the reservoir in response to a hyperglycemic glucose concentration and to prevent insulin release from the reservoir in response to a hypoglycemic glucose concentration. Thus, integration of the glucose-responsive membrane or plug with the insulin reservoir provides a device that enables continuous sensing of glucose levels in real-time and corresponding automatic adjustment of insulin release rate.

Figure 1A:
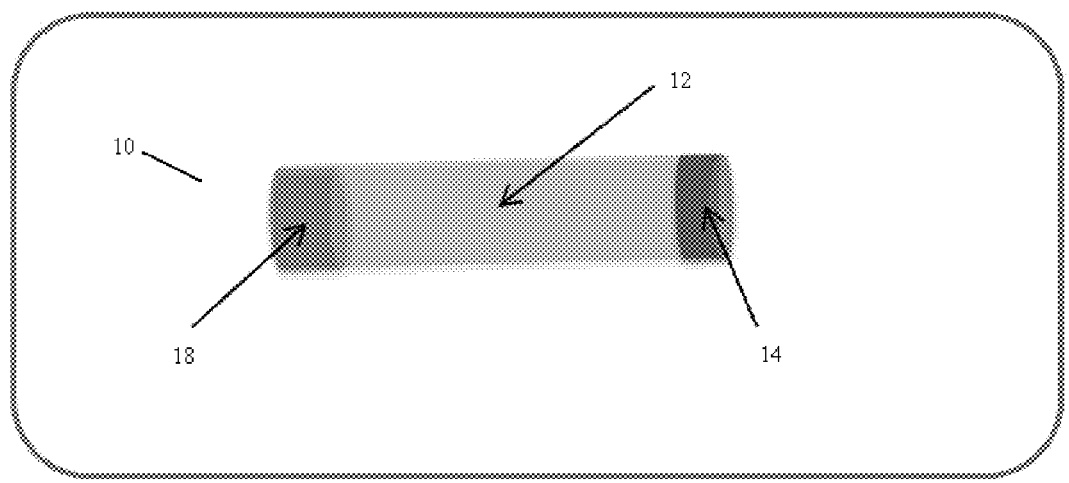
FIG. 1 is a schematic showing an insulin delivery device in accordance with an embodiment of the invention (A), and the mechanism of the glucose-responsive release of insulin across the plug (B)
Figure 1B:
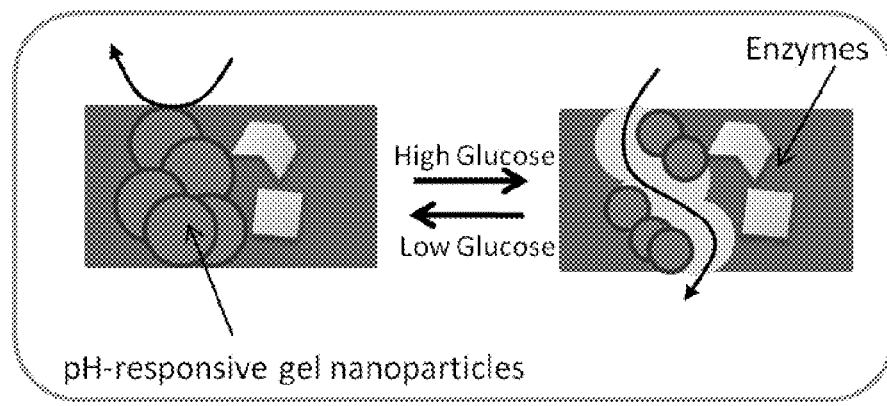

An insulin delivery device (10) in accordance with the invention is shown in FIG. 1A, comprising an insulin reservoir (12) and a glucose-responsive plug (14). If the body of the reservoir (12) is open-ended (as in the case of a tube), it may include sealing (16) at the open end thereof. Materials appropriate for such sealing include, but are not limited to, biocompatible metallic materials, inorganic materials comprising glass and ceramic, and polymers. Suitable polymers include polyvinyls, polyamides, polyurethans, silicon rubbers and acylic polymers. Examples of such polymers include poly(ethylene-co-vinyl acetate), ethylcellulose, silicone rubber and polydimethylsiloxane.

The reservoir of the device is in a form suitable to retain insulin, e.g. a tube or disk, having an opening suitable to receive the insulin-release glucose-responsive plug or membrane. The reservoir may be made of any biocompatible material, or material altered to become biocompatible, that is suitable to retain insulin. Thus, the reservoir may be made of synthetic or natural polymers such as collagen, starch blends, hyaluronic acid, alginates, carrageenan, silicone rubbers, polydimethylsiloxane, polyurethanes, acrylic polymers, poly(methyl methacrylate), polyesters, cellulose derivatives, cellulose acetate, polyethylene terephthalate, polycarbonate, polysulfone, polyvinyl chloride, polyethylene, polypropylene, polymethylacrylate and nylon. The reservoir may also be made of biocompatible metals, glass, ceramics, or hybrid materials formed with a biocompatible metal, glass or ceramics with one or more polymers. The surface of the device may additionally be functionalized to improve the safety, hydrophilicity and biocompatibility of the device, to improve adherence of the device to a plug or membrane and/or to avoid aggregation of insulin within the interior of the reservoir that may be induced by hydrophobic surfaces. Advanced surface modification techniques (e.g. silanization and PEGylation) may be applied to achieve one or more of these improvements.

The surface of the device and the membrane or plug may be modified with a non-fouling material that prevents cell adhesion. The non-fouling material may be covalently or physically bound to the surface of the device. Examples of non-fouling materials include hydrophilic polymers comprising polyethylene glycol chains of various molecular weights, and hydrophobic polymers comprising poly(ethylene-co-vinylacetate). The polymer layers may contain polyelectrolytes and immunomodulators comprising heparin and anti-inflammatory peptides.

The membrane or plug comprises a polymeric matrix having an inorganic component and a stimulus-responsive component adapted to alter the porosity of the membrane or plug in response to a stimulus, such as an increase in glucose concentration, and thereby provide regulated release of insulin.

The stimulus-responsive component comprises a composite of at least one hydrogel that shrinks or swells (resulting in increased porosity or decreased porosity, respectively) when exposed to a stimulus, such as an increase in glucose concentration, and at least one second polymer or polymer mixture that does not change (e.g. does not shrink or swell) when exposed to the same stimulus. Examples of suitable hydrogels include poly(ethylene oxide), polymers of R-acrylamide, R-acrylate and $R_1$-acrylic acid, $R,R_1,R_2$-polysaccharides, or $R,R_1,R_2$-cellulose in which R, $R_1$ and $R_2$ may be H or alkyl (e.g. $C_1$-$C_{18}$) or —COOH containing groups. Examples of a suitable second polymer include crosslinked proteins and derivatives, e.g., bovine serum albumin, ethylcellulose, methylcellulose, propylcellulose, methoxypropylcellulose, hydroxypropylmethylcellulose, cellulose acetate, cellulose nitrate, poly(vinyl alcohol), poly(vinyl chloride), polystyrene, polyethylene, polypropylene, poly(ethylene-co-vinyl acetate), polyesters, e.g., poly(hydroxybutyric acid), poly(hydroxyvalerianic acid-co-hydroxybutyric acid), poly(lactic acid), poly(glycolic acid), poly(lactic acid-co-glycolic acid), poly($\epsilon$-caprolactones), poly($\epsilon$-caprolactone-co-DL-lactic acid), polyanhydrides, e.g. poly(maleic anhydride), polyamides, albumin, gelatin, chitosan, collagen, pol(hydroxyalkyl)-L-glutamines, poly($\gamma$-ethyl-L-glutaminate-co-glutamic acid), poly(L-leucine-co-L-aspartic acid), poly(proline-co-glutamic acid), poly(orthoesters), e.g. poly(alkyl 2-cyanoacrylates), polylysine, alginate, alginic acid, polyurethanes, poly(methyl methacrylate), poly(methyl methacrylate-co-methacrylic acid), and poly(methacrylate-co-hydroxypropyl methacrylate).

Figure 2A:
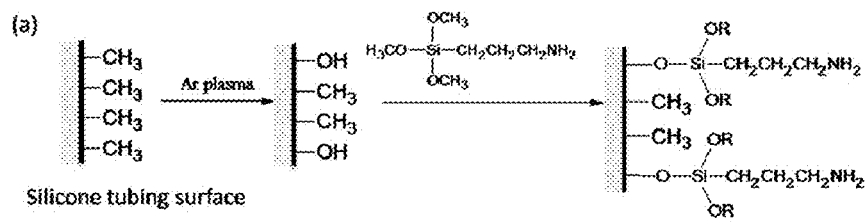
FIG. 2 is a schematic showing the reactions and steps involved in the surface modification of the device, including the silanization of the silicone tubing (A), crosslinking of the BSA-based plug with the amine groups of the silanized silicone tubing (B), the PEGylation of the device surface (C)
Figure 2B:
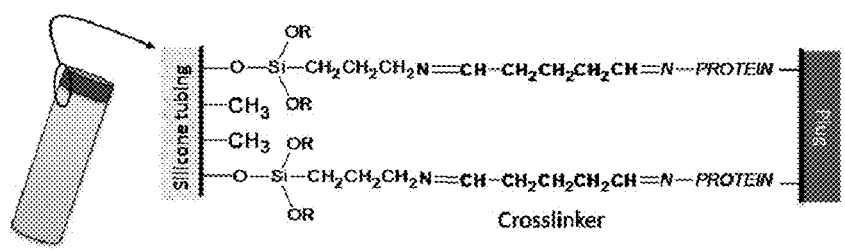

In addition, the stimulus-responsive component includes a catalytic component. The catalytic component is sufficient to catalyze the change (e.g. the shrinking or increase porosity) in the hydrogel in response to a hyperglycemic level of glucose, without any significant adverse effect on the biocompatibility of the device, that permits release of insulin from the device as shown in FIG. 2B. In one embodiment, the catalytic component comprises enzymes which catalyze the change in the hydrogel. For example, a glucose oxidase (along with any required cofactor, e.g. a flavin adenine dinucleotide (FAD) moiety) may be incorporated into the polymer matrix of the plug, to oxidize glucose, when present in hyperglycemic concentrations, which subsequently forms gluconic acid and hydrogen peroxide. The formation of gluconic acid in the presence of hyperglycemic concentrations of glucose results in a drop in pH sufficient to cause the hydrogel to shrink. Shrinkage of the hydrogel results in an increase in porosity and permits a flow of insulin from the reservoir of the device. Another enzyme, e.g. catalase, may form part of the catalytic component to break down the harmful hydrogen peroxide and regenerate oxygen that is needed for glucose oxidation. The amounts of the glucose oxidase and catalase in the glucose-responsive component may each be in the range of about 0.01% to 20% (w/w).

The inorganic component includes inorganic particles suitable at least to stabilize the structure of matrix forming the membrane or plug, and which may additionally increase the mechanical strength of the matrix forming the membrane or plug, enhance the activity and stability of the catalytic component, and may result in an increased recovery of oxygen from hydrogen peroxide as well as dampen the pH decrease at normal glucose levels, and/or may facilitate quenching of hydrogen peroxide. Examples of such inorganic particles include, but are not limited to, metals and their oxides, e.g. $MnO_2$, Mn, Ag, Au, $SiO_2$, titanium, iron, magnesium, silica-based materials, and carbon-based nanomaterials such as carbon nanotubes. The inorganic particles have particle sizes ranging from about 1 nanometer to about 1-10 millimeters. The inorganic particles are generally added to the composite in an amount in the range of about 0.01%-20% (w/w). The weight ratio of inorganic component:glucose oxidase:catalase may vary from about 0.1:0.1:1 to about 10:10:1. The inorganic particles may be coated by another inorganic material (e.g. such as metals and their oxides), organic material, or a polymer (e.g. polyelectrolytes, albumin) to improve their stability and biocompatibility.

The device regulates the rate of insulin release in response to glucose concentration. When glucose levels are normal (e.g. around 100 mg/dL), the production of gluconic acid is largely compensated by the medium buffering, the diffusion of gluconic acid, and the action of the inorganic component. As a result, the pH inside the membrane is close to the pH of the medium (i.e. pH of at least about 7.0). At this pH, the hydrogel component is in a swollen state, the membrane has low porosity and thus insulin release is slow. On the other hand, in the presence of hyperglycemic glucose levels (200-400 mg/dL), greater glucose oxidation results in a drop in pH that triggers the hydrogel component of the device membrane to shrink and increase porosity in the membrane, thereby resulting in insulin release. On release of insulin, the glucose levels return to normal within a period of time, resulting in a decrease in production of gluconic acid, a rise in local pH and subsequent expanding of the stimulus-responsive hydrogel component to prevent further insulin release. The glucose-regulated insulin release profile of the device is, thus, based on the reversible pH-sensitivity of the hydrogel component in the membrane or plug.

A method of preparing a glucose-responsive membrane/plug is also provided in another aspect of the invention. The method includes the steps of combining the inorganic component, at least one polymer that does not change dimension when exposed to a stimulus (e.g. increase in glucose concentration) and the catalytic component(s), adding at least one hydrogel that changes dimension when exposed to a stimulus to form a mixture, and then incubating the mixture with a cross-linking agent (e.g. such as glutaraldehyde or genipin) under conditions suitable to permit cross-linking and formation of the membrane. As one of skill in the art will appreciate, the cross-linking agent will be added in an amount suitable to render a membrane/plug in which the cross-linking density is appropriate to permit porosity changes in the membrane and to allow insulin release in response to a stimulus.

The reservoir, formed from a biocompatible material as described, may be prepared for attachment to the glucose-responsive plug. Functionalization of the surface of the reservoir may facilitate firm attachment of the plug or membrane to the reservoir. For example, silanization to introduce groups (e.g. amino groups) suitable for crosslinking with reactive groups on the surface of the plug or membrane may facilitate such attachment. The attachment of the plug or membrane to the reservoir may be achieved after the plug or membrane is formed or simultaneously with the formation of the plug or membrane. If the reservoir is open-ended, then it may be sealed as described above with appropriate materials. Finally, the device, including reservoir and plug, may be surface modified to optimize biocompatibility, for example, by PEGylation in a manner known in the art.

The present insulin delivery device is shaped to be suitable for implantation into a mammal to be treated. Thus, the device may be formed into various shapes and structures including cylindrical, spherical, disk-shaped or sheet-like. Generally, the dimensions of the device are no more than about 10 cm long, and preferably no more than about 5 cm long, and no more than about 5 cm wide. The size of the device will determine the volume of insulin that may be contained in the device. As one of skill in the art will appreciate, a smooth outer surface will facilitate implantation and use of the device.

Prior to implantation into a mammal, the device is filled with an insulin formulation, by injection, insertion or other suitable means, which may be in the form of a liquid, semi-solid or solid at body temperature. The insulin may be dissolved in a solution, dispersed in a suspension or paste, or dispersed within a solid matrix of a polymer, lipid, or an inorganic material. Such dispersed insulin particles generally dissolve gradually by liquid that penetrates the solid matrix and can be released through the glucose-responsive membrane or plug when the membrane is triggered to increase porosity. Further, as one of skill in the art will appreciate, insulin may be present in the formulation as a monomer, dimer or hexamer. Metal ions, e.g. $Zn^{2+}$, $Mn^{2+}$, $Cu^{2+}$, $Ca^{2+}$ or $Co^{2+}$, may be added to the insulin formulation in a range of about 0.01-0.25 mg/units to modulate the assembly and stability of insulin. In the liquid form, insulin may be dissolved in slightly acidified or neutral buffers, e.g. in normal saline solution, citrate, acetate, phosphate, Tris-HCl, Glycine-HCl, HEPES, HEPPS, or in a combination of two or more buffers. Non-ionic surfactants or water soluble polymers, such as sodium dodecyl sulfate, pluronics, dodecyl maltoside, glucopyranosides, sorbitans, polysorbates, poly(lactide-co-glycolide), albumin, polyvinyl alcohol, block copolymers, or a combination thereof, may be added to the preparation to improve insulin stability and solubility. Insulin particles may be prepared by free-drying in the presence of sugar, surfactant or polymers that stabilize the insulin. The insulin particles may also be encapsulated in a gel using polymers and hydrogels, e.g. albumin, collagen, alginate, chitosan, polyacrylamide, gelation, arabic gum, starch and the like. In the solid or semi-solid formulations, the insulin particles may be dispersed in powders, in nano- or microparticulate form, with or without polymers, surfactants or any other stabilizer or dispersing material. Solid preparations may be compacted into different shapes, e.g. pallets, disks, sticks, rods and the like.

The insulin delivery device is useful in a method of treating Type 1 and Type 2 diabetes in mammals, including human and non-human mammals (animals). In this regard, one or more devices according to the invention may be implanted into a mammal in need of treatment for diabetes, either subcutaneously or intraperitoneally. Multiple devices may be implanted at different locations in the mammal, or at the same location in various arrangements, e.g. side-by-side, stacked, or bound by a mesh, glue or screws. As used herein, the terms "implant" or "implantation" are used to refer to the insertion or grafting of the insulin delivery device, either wholly or partially, into tissues, under the skin, or a body cavity. Implantation may be achieved using well-established techniques in the art.

Once implanted, the device functions to deliver insulin at a elevated rate in hyperglycemic conditions and may also provide basal release of insulin under normal glycemic conditions. As one of skill in the art will appreciate, replacement frequency of the device will vary on a number of factors, including but not limited to, the specifications of the device, number of refills and the insulin requirements of the mammal into which the device is implanted.

The release profile of the device may be delayed on implantation by coating the insulin-releasing membrane with a layer of biodegradable material, e.g. poly(lactide-co-glycolide), polyesters, polyanhydrides, gelatin or collagen. This is particularly useful when multiple devices are implanted into a single mammal. A first device may be uncoated and have an undelayed release profile, while the additional devices may be coated with varying amounts of biodegradable material to result in staged release of insulin by each device, one after the other. In this way, the frequency of replacing an empty implanted device with an insulin-filled device, or refilling of the device with a fresh insulin formulation, is reduced thus decreasing the stress on the mammal being treated with the implants.

Broadly stated, the present invention relates to a closed-loop glucose sensitive insulin delivery system that mimics the pancreatic function of blood glucose homeostasis with the design and fabrication of a prototype implantable device. The device is ideal for treatment of diabetes as it overcomes the limitations of insulin injection therapy and provides a means to better manage the disease.

Embodiments of the invention are described by reference to the following specific examples which are not to be construed as limiting.

Example 1

Synthesis of Hydrogel Nanoparticles

Poly(N-Isopropylacrylamide-co-methacrylic acid) (poly(NIPAM/MAA)) nanoparticles were synthesized by an aqueous dispersion polymerization process. NIPAM, MAA and N,N'-Methylene-bis-acrylamide (BIS), at a mole ratio of 1:1:0.068 were dissolved in DDI water giving a total concentration of 135 mM. Sodium dodecyl sulphate (SDS) at a concentration of 0.4 mM was added to stabilize the nanoparticles produced. The mixture was purged with $N_2$ and then potassium persulfate (2.1 mM) was added to initiate the polymerization. The reaction was carried out at 70° C. under $N_2$ atmosphere and stirring at 200 rpm for 4 h. The obtained nanoparticles were purified by membrane dialysis (molecular weight cutoff 12,000 to 14,000, Fisher Scientific) against DDI water. The diameter of the hydrogel nanoparticles was determined to be about 380±110 nm in pH PBS solution pH 7.4 (0.01M phosphate; 0.15M NaCl); 157±50 nm in PBS solution pH 5.0 (0.01M phosphate; 0.15M NaCl) and 325±109 when the pH was increased to 7.4 again. The size distribution was determined by dynamic laser light scattering.

Example 2

Synthesis and Characterization of $MnO_2$ Nanoparticles

The sonochemical reduction of permanganate with manganese ions was used to prepare $MnO_2$ nanoparticles (NPs). In brief, a potassium permanganate aqueous solution (5 mL, 0.05 mM) was kept under ultrasonic field for 30 s by using an ultrasonic processor probe operating at approximately 50 Hz (Heischer UP100H, Germany). Manganese acetate aqueous solution (1 mL, 0.07 mM) was added and the dark brown dispersion obtained was sonicated for an additional 30 s. Solid nanoparticles were isolated by ultracentrifugation, thoroughly washed with DDI water, and freeze-dried overnight. Prior to use, powdered $MnO_2$ NPs were redispersed in DDI water or PBS solution (20-30 $mg.mL^{-1}$) by ultrasonication (1 min/50 HZ) followed by stirring overnight.

Figure 3:
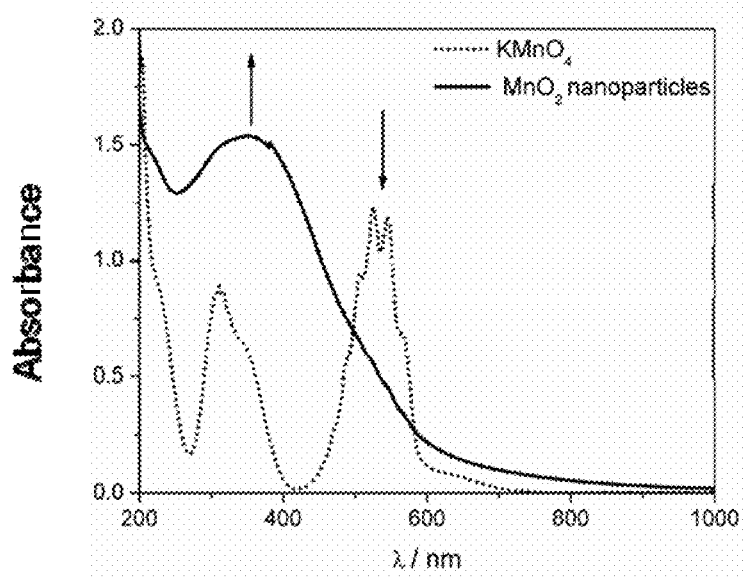
FIG. 3 shows UV spectra of reactant $KMnO_4$ and prepared $MnO_2$ nanoparticles.

Characterization of $MnO_2$ NPs was initially carried out from absorbance studies. The UV-Vis spectrum of the golden brown colloidal dispersion obtained is shown in FIG. 3. After the reaction with manganese acetate the three peaks centered at 315 nm, 525 nm and 525 nm originated from $KMnO_4$ disappeared and new broad peak at 360 nm, a characteristic of colloidal $MnO_2$ was observed, indicating the formation of $MnO_2$ NPs. TEM images of the $MnO_2$ nanoparticles revealed small discrete nanoflakes with an average size of about 80 nm.

Example 3

Preparation and Characterization of Glucose-Responsive Membranes

Membranes were prepared by crosslinking BSA with glutaraldehyde in the presence of 30 wt. % poly(NIPAM/MAA) NPs and various amounts of enzymes and $MnO_2$ NPs as follows:
(i) membrane 1: 5 wt. % GOx; (ii) membrane 2: 5 wt. % GOx and 10 wt. % $MnO_2$ NPs
(iii) membrane 3: 5 wt. % GOx and 1.6 wt. % CAT (CAT/GOx=0.29 w/w) and (iv) membrane 4: 5 wt. % GOx, 1.6 wt. % CAT and 10 wt. % $MnO_2$ NPs. In a typical preparation, to a small vial containing 6 mg of powder $MnO_2$ NPs dispersed in 200 μL of pH 5.0 PBS solution, 28 mg of BSA, 3 mg of GOx and 0.86 mg of CAT were introduced and incubated at 37° C. for 10 min. Following the addition of 85 μL of a 200 $mg.mL^{-1}$ dispersion of poly(NIPAM/MAA) NPs in DDI water, the mixture was stirred for 10 min, and then 15 μL of glutaraldehyde (grade I, 25%) was introduced. The mixture was quickly spread on a glass slide (~3.5×2.0 cm) and allowed to cross-link at room temperature for 1 h. The obtained membrane with approximately 400 μm in thickness was rinsed with DDI water, soaked in pH 7.4 PBS solution and kept at 4° C.

Determination of Mechanical Properties of Membranes

The stress-strain curves of wet membranes were measured using an Instron 3366 (USA). As-prepared membranes with dimensions of 50×25×0.8 mm were soaked in pH 7.4 PBS 24 h before measurements. Tests were carried out at 20° C. and ca. 50% relative humidity with a tensile speed of 0.5 mm/min and initial gauge length at 20 mm. The Young's modulus of elasticity was determined from the slope of the linear portion of the curves.

TEM, ESEM and SEM Measurements

Transmission electron microscopy (TEM) images of $MnO_2$ NPs were performed on a Hitachi H7000 microscope (Japan) at 75 kV. The $MnO_2$ colloidal dispersion was dropped on a charged copper grid. Environmental scanning electron micrographs (ESEM) were obtained in a Hitachi S3400 microscope (Japan) at 15 kV. As-prepared wet membranes were mechanically fractured, directly fixed onto a cold stage sample holder with double-sided carbon tape and frozen at −24.0 under 90 Pa. SEM images were obtained in a Hitachi S-3400N microscope (Japan) at 5-10 kV. Membrane samples were fractured in liquid nitrogen and dried at the critical point with liquid $CO_2$ in an Autosamdri-810 apparatus (Tousimis Research Corporation, USA). Samples were directly fixed onto the sample holder with double-sided carbon tape and coated with gold.

Figure 6:
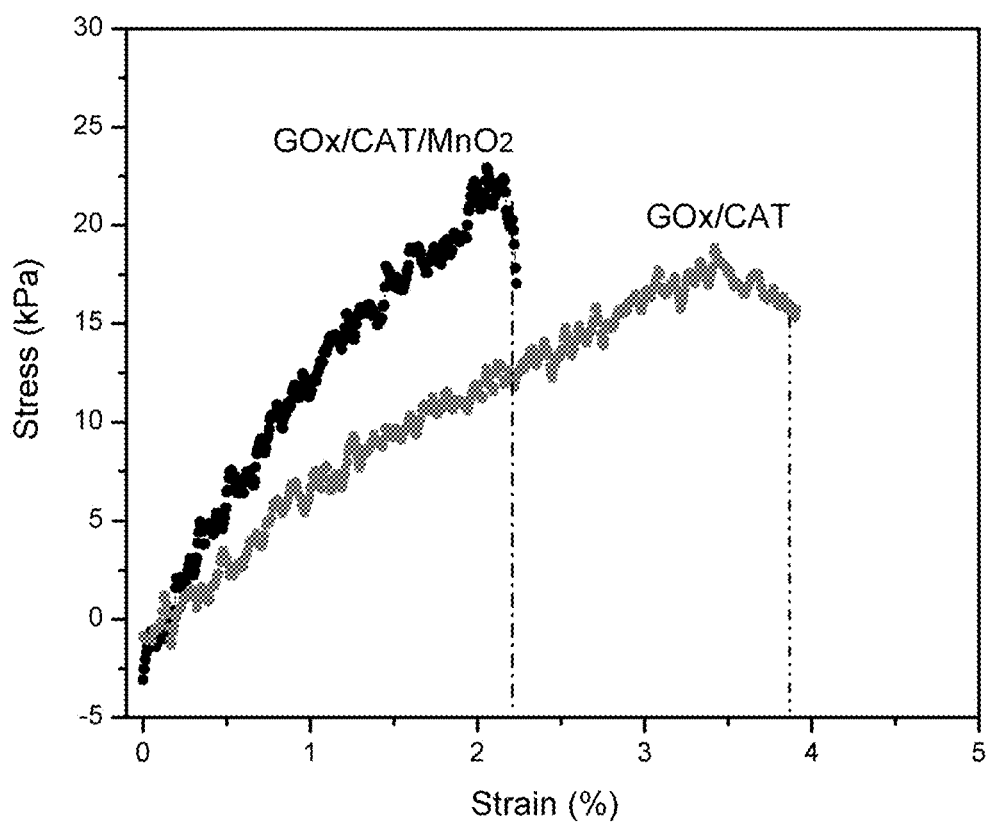
FIG. 6 graphically compares stress-strain curves of membranes with or without incorporated $MnO_2$ nanoparticles.

The mechanical strength and rigidity of the membrane is increased significantly due to the interaction of $MnO_2$ nanoparticles with the protein (FIG. 6). This interaction also resulted in more uniformly distributed rigid pores which allow the pH-sensitive nanoparticles to swell or shrink freely in response to changes in glucose concentration.

Example 4

Determination of Activity and Stability of the Immobilized GOx

The activity of immobilized GOx for oxidation of glucose was determined by using a glucose assay kit (HK-Sigma) in the presence of $MnO_2$ nanoparticles or CAT. At determined times, 10 μL of the medium was taken and added to 100 μL of assay kit, incubated for 15 min at room temperature and assayed using a microplate reader (Molecular Device, USA) at 340 nm. The amount of $H_2O_2$ produced by GOx-immobilized membranes or the amount of $H_2O_2$ quenched by CAT, $MnO_2$ nanoparticles or CAT with $MnO_2$ nanoparticles was measured by using PeroXOquant™ assay kit (Pierce, USA). Individual membranes (10×10×1 mm) were prepared containing a fixed amount of GOx=1 mg. Samples were soaked in 20 mL of 200 $mg.dL^{-1}$ glucose solution in pH 7.4 PBS solution and incubated at 37° C. At predetermined times, 10 μL of the medium was taken and added to 100 μL of assay kit, incubated for 15 min at room temperature and assayed using a microplate reader at 595 nm. Both assay kits were used according to the manufacturer's instructions.

Figure 4A:
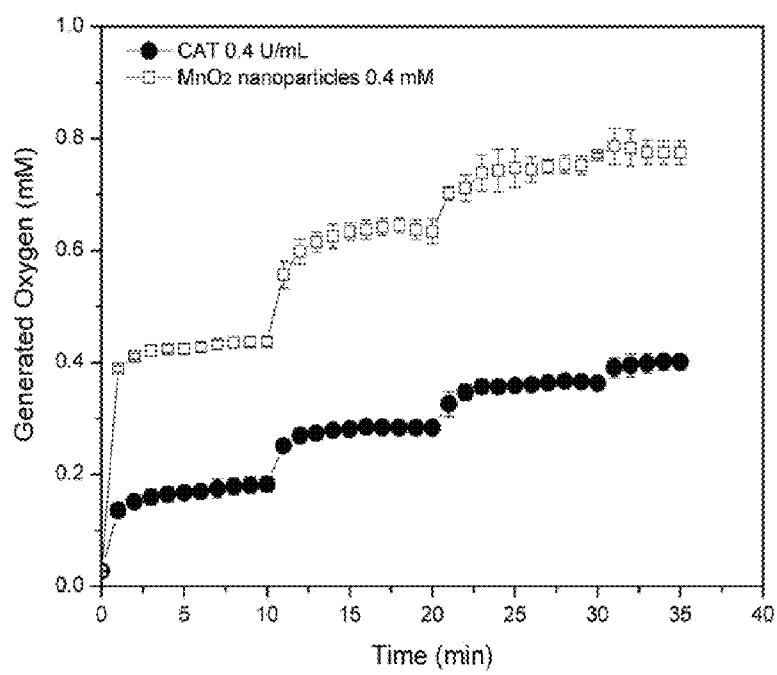
FIG. 4 graphically illustrates the effects of $MnO_2$ nanoparticles and catalase (CAT) on oxygen production (dissolved oxygen) from decomposition of $H_2O_2$ (A), and $H_2O_2$ generation in the presence of composite membranes containing immobilized GOx/CAT or GOx-CAT/$MnO_2$ nanoparticles (B)
Figure 4B:
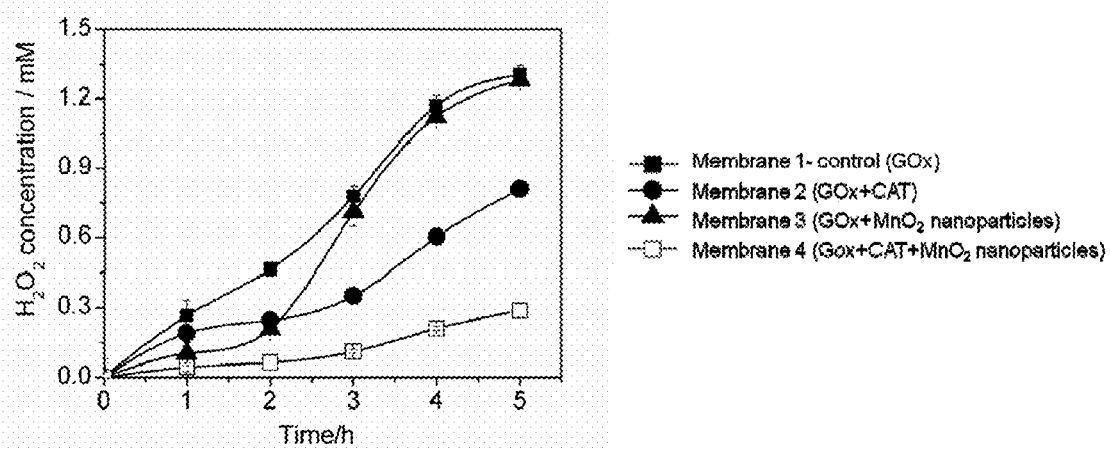

FIG. 4A shows that oxygen generation is increased in the presence of $MnO_2$ nanoparticles in comparison to the CAT alone. In addition, membranes incorporating CAT with $MnO_2$ nanoparticles exhibited greater $H_2O_2$ quenching activity than membranes with either alone (FIG. 4B).

Figure 5:
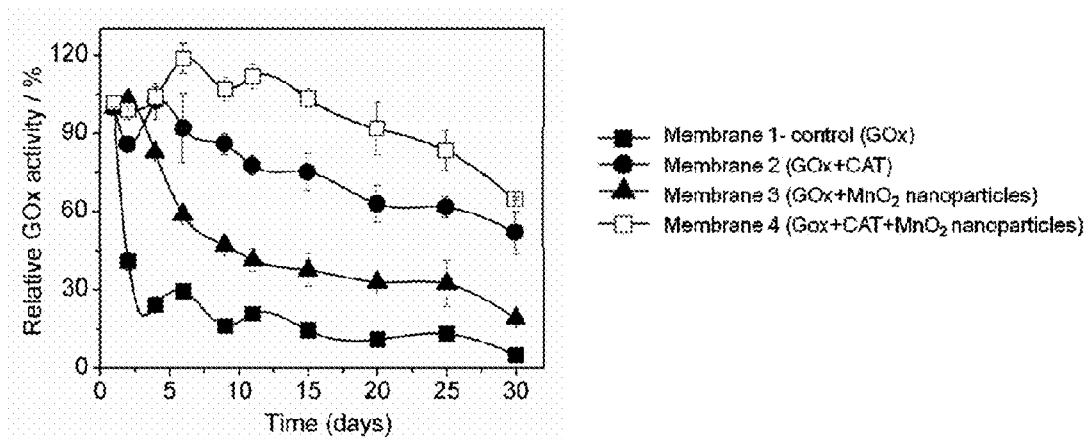
FIG. 5 graphically illustrates the relative activity of GOx in a membrane containing CAT, $MnO_2$ nanoparticles or CAT with $MnO_2$ nanoparticles.

The pH decrease of a glucose solution, another measure of GOx enzymatic activity and its relative stability during storage, was also determined by checking the ability of GOx to lower the pH of a glucose solution. Membranes with a dimension of 10×10×1 mm, each containing a 1 mg of GOx, were soaked in 5 mL of 200 mg.dL$^{-1}$ glucose solution in normal saline (NaCl 0.15M with pH adjusted to 7.4). Freshly prepared samples or samples stored in pH 7.4 PBS solution at 4° C. for various time periods up to 30 days were incubated at 37° C. and the pH of the solution was measured as a function of time. The slopes of the linear portion of the curves were calculated. The relative activity (RA) of immobilized GOx was calculated according the following equation:

$$RA\ (\%) = \frac{St \times 100}{St1}$$

where St1 and St are respectively the slope of the pH changes curve at time day 1 and at time day t. The results are illustrated in FIG. 5 showing that membranes incorporating CAT with MnO$_2$ nanoparticles exhibited greater relative GOx activity than membranes with either alone.

Example 5

Insulin Permeation Across Glucose-Responsive Membranes

The permeation of insulin through the membranes in response to glucose concentration was carried out using a horizontal side-by-side diffusion cell system (PermeGear, Inc., USA) at controlled temperature (37° C.). The receptor cell was filled with pH 7.4 PBS solution containing 0.02 mM of Pluronic F-68 and 100 mg.dL$^{-1}$ of glucose and the donor cell was filled with 1 mg.mL$^{-1}$ bovine insulin solution in the same medium. The initial glucose concentration in all experiments was 100 mg.dL$^{-1}$. Aliquots of highly concentrated glucose solution (20 g.dL$^{-1}$) were then added to increase the glucose concentration to 200 and/or 400 mg.dL$^{-1}$ after a predetermined time. The solution in the receptor cell was continually pumped to a UV-flow cell and the insulin permeation was determined by measuring insulin absorbance at γ=276 nm using an UV spectrophotometer (HP 8453 UV Spectrophotometer, USA). The slope of the curves was calculated and the permeability of insulin (P) (cm$^2$.s$^{-1}$) was calculated according the following equation:

$$P = \frac{\text{slope of the Permeated Insulin curve}(mg.s^{-1}) \times \text{membrane thickness}(cm)}{\text{Insulin concentration in the donor cell}(mg.cm^{-2}) \times \text{area of permeation}(cm^2)}$$

The glucose-responsiveness of membrane permeability was defined as the ratio of insulin permeability measured at glucose=200 and 400 mg.dL$^{-1}$, to that at 100 or 200 mg.dL$^{-1}$, i.e., $P_{200}/P_{100}$; $P_{400}/P_{100}$; $P_{400}/P_{200}$.

To determine the regulated profile of insulin release after each cycle the membrane was kept in the diffusion cell. Solutions in both cells were removed, the apparatus was rinsed with pH 7.4 PBS solution, and fresh solutions were added in the donor cell (Insulin 1 mg.mL$^{-1}$ in the medium) and the receptor cell (just medium). Glucose concentration was alternated every 2 h between 100 and 400 mg/dL$^{-1}$ in five consecutive cycles.

Figure 7A:
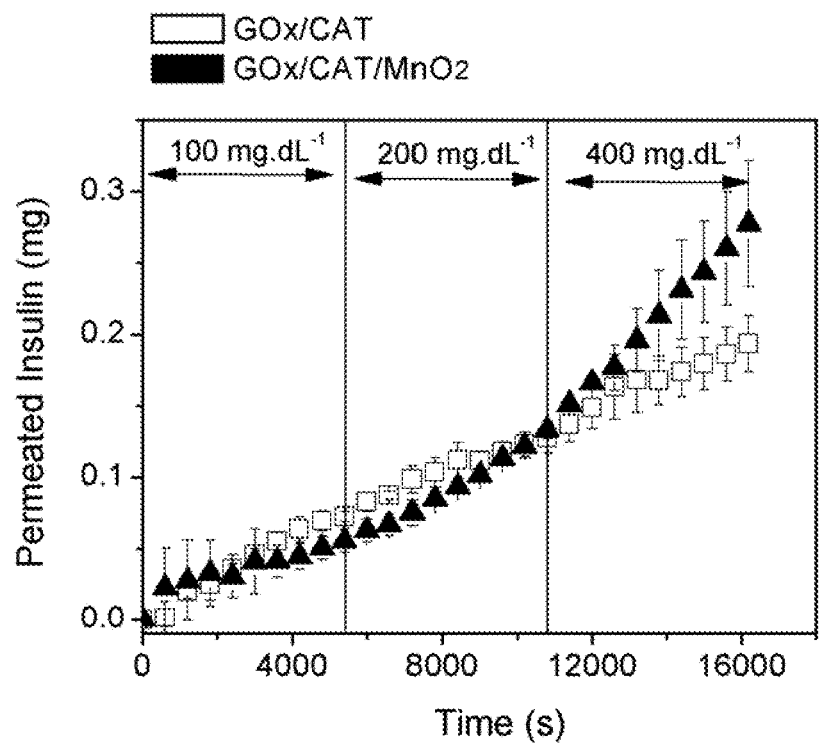
FIG. 7 graphically illustrates the profile of insulin permeation across membranes containing immobilized GOx/CAT or GOx/CAT/$MnO_2$ nanoparticles in response to step-wise change of glucose concentration (A), and insulin permeability as a function of glucose concentration (B)
Figure 7B:
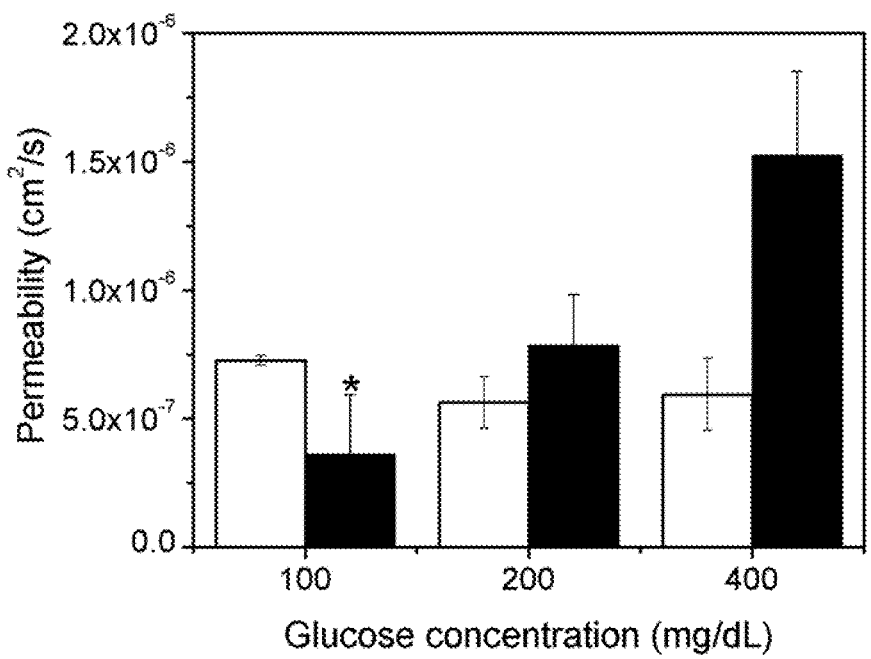

The glucose-responsive insulin release across the membranes is compared in FIG. 7. For the membrane containing MnO$_2$ nanoparticles, the rate of insulin permeation increases with increasing glucose concentration. The permeability of insulin, calculated from the slopes of the curves presented in FIG. 7a, is significantly higher at higher glucose concentrations at 200 mg/dL and 400 mg/dL than at 100 mg/dL for the membrane with MnO$_2$ nanoparticles, while the permeability of the membrane without MnO$_2$ nanoparticle remains steady (FIG. 7b). For the membrane containing MnO$_2$ nanoparticles, the permeability of insulin increases about two-fold when glucose is increased from 100 to 200 mg.dL$^{-1}$ and from 200 to 400 mg.dL$^{-1}$ ($P_{200}/P_{100}$ and $P_{400}/P_{200}$=2.18 and 1.95, respectively ($p<0.05$)), and about four-fold when the glucose concentration is increased from 100 to 400 mg.dL$^{-1}$ ($P_{400}/P_{100}$=4.23 ($p<0.05$)).

The superior mechanical and morphological properties imparted by MnO$_2$ nanoparticles led to glucose-dependent insulin release across the membrane.

Example 6

Preparation of an Insulin Delivery Device

The insulin delivery device was prepared in five steps as follows:

Step 1—Surface Modification of Silicone Tubing:

Silicone tubing (length=3 cm) was oxidized for 20 min in a 5 W air plasma and then immersed in 0.1M 3-aminopropyltrimethoxysilane in anhydrous ethanol overnight. Silanized tubing was extensively rinsed with ethanol and blow-dried with nitrogen gas at room temperature. In this process the surface hydroxyl groups, generated by oxidation with air plasma, were reacted with a trialkoxysilane derivative. The condensation between grafting molecules and surface groups generate highly stable Si—O—Si bonds creating a functional self-assembled monolayer on the surface, which can consist of aminopropyl or any other silane derivative (FIG. 2A). The chemical composition of silicone tubing before and after silanization, as determined by X-ray photoelectron spectroscopy (XPS) reflects a clear alteration in the surface chemical composition after the silanization. In the XPS analysis, a strong N1s signal was observed for the silanized tubing (% N=1.13). This signal was not visible on the blank silicone (% N=0.00), indicating that the aminopropyl groups are successfully coupled to the tubing surface in an order of magnitude comparable with the depth of information of XPS, i.e. 5-10 nm. The silanization step increases the hydrophilicity of the tubing surfaces to prevent insulin aggregation in the reservoir. Also, the functionalization with amine groups allows for the direct crosslink of the glucose-responsive plug with the tubing surfaces.

Step 2—Crosslinking of the Glucose-Responsive Plug with Silanized Silicone Tubing:

One end of the silanized tubing was sealed with a glucose-responsive plug as follows. In a small vial, powder inorganic nanoparticles (e.g. nano-MnO$_2$) (6 mg) were dispersed in pH 5.0 phosphate buffer (200 μL). Then, bovine serum albumin (28 mg), glucose oxidase (3 mg) and catalase (0.86 mg) were dissolved in the dispersion by incubating 10 min at 37° C. pH-responsive hydrogel nanoparticles were added (85 μL, 200 mg.mL$^{-1}$ dispersed in DDI water) and the mixture was stirred 10 min. Then, glutaraldehyde 25% (15 μL) was added and the mixture (2.5 μL) immediately transferred to one end of the tubing. The obtained plug was crosslinked at room temperature for 30 h, then rinsed with DDI water and soaked in pH 7.4 phosphate buffer overnight at 4° C. The glucose-responsive plug was prepared by the crosslink of proteins with glutaraldehyde in the presence of the pH-responsive hydrogel nanoparticles, inorganic nanoparticles and enzymes. The crosslink process occurs inside one end of the silanized silicone tubing leading to a plug at about 1 mm in thickness. Since amine groups were introduced on the tubing surface, the covalent coupling of the protein-based plug with the silanized tubing occurs as shown in FIG. 2B.

Step 3—Polymer Sealing:

The open end of the tubing was dipped in a polymer solution, (e.g. ethylene-vinyl acetate copolymer resin solution 8% in dichloromethane (w/v)) and immediately blow-dried with air for approximately 1 min. The procedure was repeated at least 10 times until a round coating was obtained.

Step 4—Coupling of PEG Derivative (PEGylation)

Figure 2C:
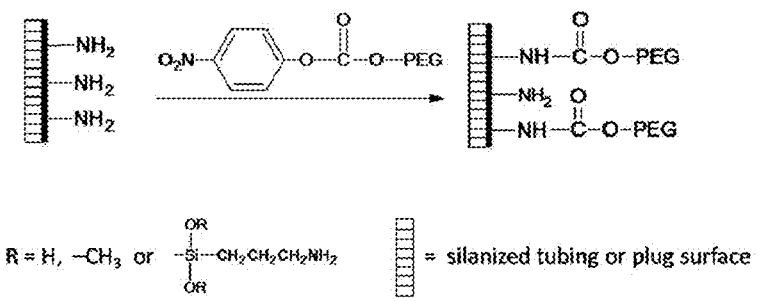

Devices were soaked in 0.01M of activated PEG (poly (ethylene glycol)) in pH 7.4 phosphate buffer for 48 h at 4° C. Devices were extensively washed with DDI water and kept in pH 7.4 PBS at 4.0 prior to use. Coupling of PEG was accomplished through the amide bond formation between COO of activated PEG and $NH_2$ of protein molecules present on plug surface (FIG. 2C). Since amine groups were introduced on tubing surface through the silanization process, the coupling of activated PEG with the aminopropyl groups on silicone surface also occurs. Characterization of the products by NMR shows the characteristic peak for PEG at 4.4 ppm suggesting that the PEGylation of the plug and silanized tubing is successfully achieved.

Step 5—Insulin Formulation

Insulin stock solution: The device was filled with highly concentrated neutral buffered insulin solution. e.g. insulin (25 mg) and n-octyl-β-D-glucopyranoside (3.65 mg) were dissolved with 0.1M NaOH aqueous solution (600 μL). (4-(2-hydroxyethyl)-1-piperazineethanesulfonic acid (HEPES) was added (12.6 mg) and the volume brought to 1 mL by slowly adding 0.1M HCl aqueous solution. Devices were filled with this solution (≈50 μL, 1.25 mg insulin per device) by using a syringe with a thin needle. Air bubbles were avoided by piercing a second needle in the opposite side of the device.

Insulin Gel Formulation:

Insulin gel formulation was prepared using an in situ solubilization method. Human recombinant insulin and Pluronic F127 were dissolved in a glass vial with 0.1M NaOH solution to give a concentration of 100 mg/ml and 2.5 mg/ml, respectively. After both insulin and surfactant were dissolved completely, pH was adjusted to ~8 by dropwise addition of 5 μl 1M HCl, with slow agitation to redissolve precipitates between additions. Pluronic F127 was increased to 25% and 1% hydroxypropyl methylcellulose (HPMC) was added to increase viscosity. Insulin gel formulation was kept at 4° C. until both Pluronic F127 and HPMC dissolved. Devices were filled with this solution (≈50 μL, 5 mg insulin per device) by using a syringe with a thin needle Gelation was induced by incubation of the device at 37° C.

Microcrystalline Insulin:

Microcrystalline Insulin was prepared by a polythermal method. Powder human insulin (10 mg) was added to a 20-mL glass scintillation vial containing Pluronic F-68 or F-127 (0.003 g). Then, 0.02M HCl solution (2.5 mL) and 20 wt % $ZnCl_2$ solution (12 uL) were added to the vial and a clear insulin solution was obtained. Insulin was then precipitated at its isoelectric point by adding a 0.2 M sodium citrate solution (500 uL). The turbid solution was quickly heated to 50° C. in a water bath to afford a clear solution. Slow cooling of this solution to room temperature overnight afforded well-defined microcrystalline Zn-insulin. In a next step, crystals were allowed to set; the supernatant was carefully removed and the crystals were re-suspended at desired concentration (50-100 mg/mL) with a stabilizing solution containing $ZnCl_2$ 0.05 wt. % and methylparaben 0.1 wt. % with pH adjusted to 7.4. Crystals without Pluronic were prepared in a similar way except that pluronic was omitted.

Example 7

In Vitro Insulin Release from the Insulin Delivery Device

Figure 8A:
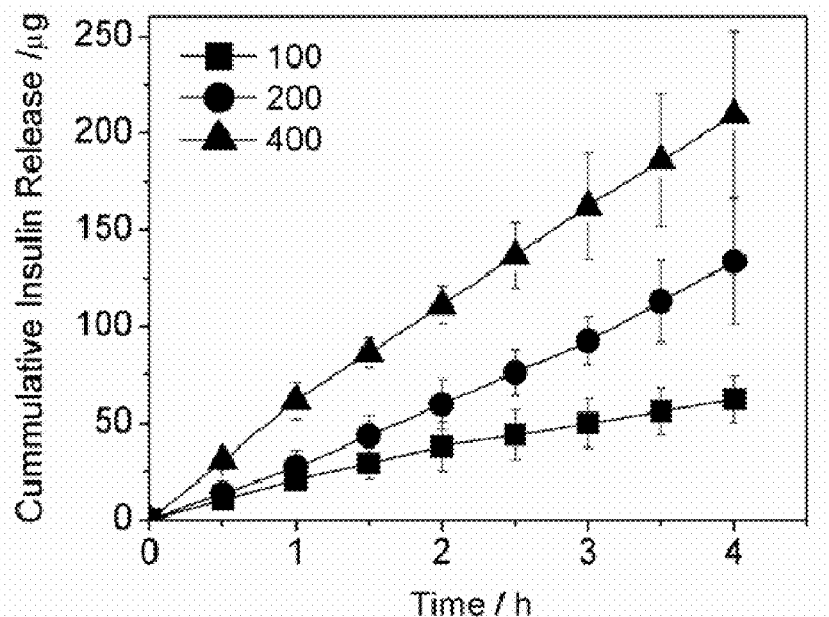
FIG. 8 graphically illustrates in vitro release of insulin from a device over time at glucose concentrations of 100, 200 and 400 mg.dL$^{-1}$ (A), the rate of insulin release ($\mu$g.h$^{-1}$) from the device as a function of glucose concentration (B) and an insulin release profile of the device as glucose concentration was alternated between 100 and 400 mg.dL$^{-1}$ in four cycles (C). Data points represent mean±SD (n=3-5)
Figure 8B:
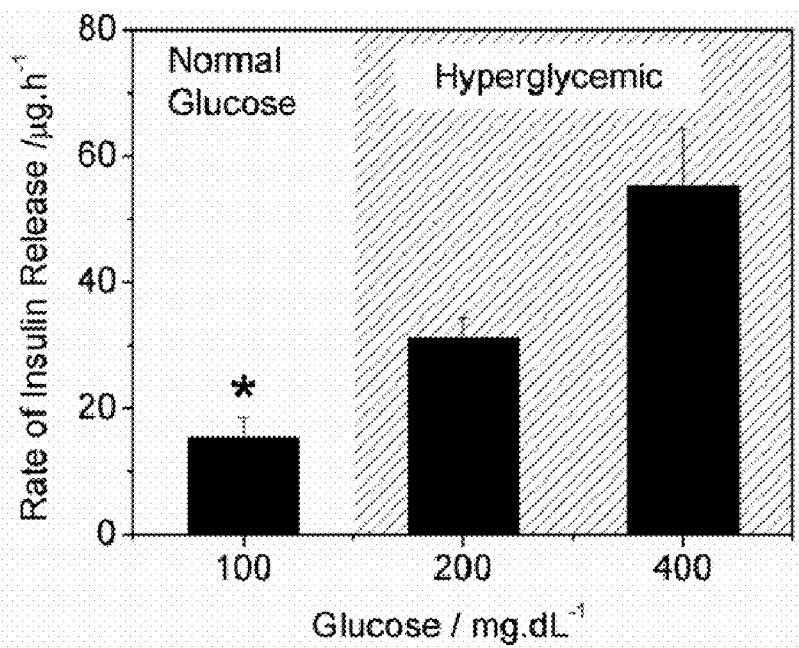
Figure 8C:
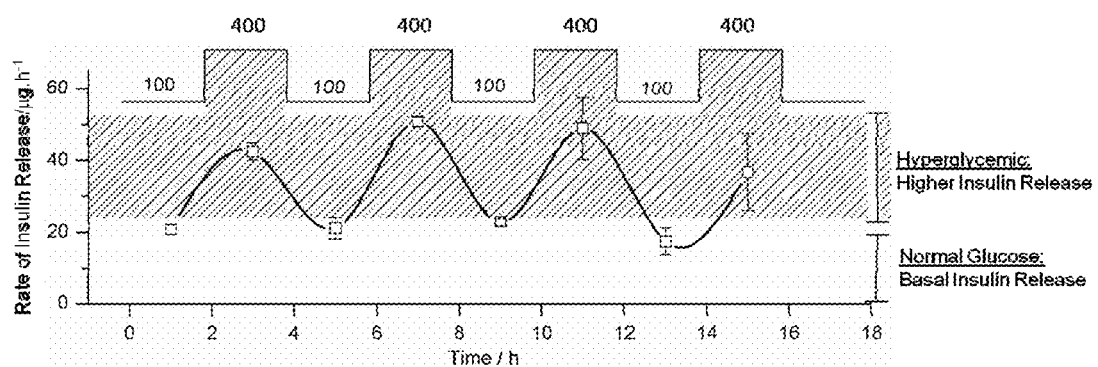

In vitro release of insulin was determined over time as a function of glucose concentration. Devices were individually placed in glass vials containing the release medium (3 mL of pH 7.4 phosphate buffer containing glucose 100 mg.dL$^{-1}$ and Pluronic F-68 0.02 mM). Vials were sealed and kept under constant mixing in a hematology mixer. The release medium was replaced every 1 h and the insulin release was determined by measuring insulin absorbance manually in a UV/VIS spectrophotometry every 15 min at γ=276 nm. The rate of insulin release was determined by the slope of the curves. The experiment was repeated with the same devices using glucose concentrations=200 and 400 mg.dL$^{-1}$ in the release medium. For each set of experiments, the devices were refilled with fresh insulin solution in order to guarantee the same concentration of insulin in the devices in all experiments. The glucose-responsiveness of the insulin delivery device was defined as the ratio of the rate of insulin release (R) determined at hyperglycemic glucose (i.e., 400 mg.dL$^{-1}$), to that at normal glucose (100 mg.dL$^{-1}$), i.e., $R_{400}/R_{100}$. As observed from the plots (FIG. 8), a relative higher rate of insulin release was obtained at hyperglycemic glucose levels. The rate of insulin release increased about two-fold when glucose in the release medium was increased from 100 to 200 mg.dL$^{-1}$ and 200 to 400 mg.dL$^{-1}$ ($R_{200}/R_{100}$ and $R_{400}/R_{200}$=2.1 and 1.8, respectively ($p<0.05$)).

To check the regulated profile of insulin delivery device in response to alternated changes in glucose concentration, devices were individually placed in glass vials containing the release medium described above. Vials were sealed and kept under constant mixing in a hematology mixer. After 2 h the glucose concentration in the medium was increased to 400 mg.dL$^{-1}$. The same procedure was repeated for subsequent alternated cycles. As demonstrated (FIG. 8), the insulin release profile of the device exhibited a pulsatile pattern when glucose concentration was alternated between normal (100 mg.dL$^{-1}$) and hyperglycemic levels (400 mg.dL$^{-1}$) in several cycles. The device responded quickly to changes in glucose level in the release medium. A three-fold increase in the insulin release rate was observed when the glucose concentration was increased to a hyperglycemic level. Additionally, the insulin release rate decreased to the initial rate when the glucose concentration was decreased to the normal level, demonstrating the glucose-regulated profile of the insulin delivery device. Also, the plots clearly show that the device presents a basal insulin release rate (about 20 μg.h$^1$) at normal glucose levels, what is highly desirable in insulin therapy.

The glucose-regulated insulin release profile of the device is based on the reversible pH-sensitivity of the bio-inorganic glucose-responsive. The plug consists of a porous bio-inorganic polymeric matrix embedded with pH-responsive hydrogel nanoparticles and the enzymes, glucose oxidase and catalase. In this system the porosity of the plug is increased at hyperglycemic glucose levels in response to enzymatic oxidation of glucose to gluconic acid, which leads to the shrinkage of the hydrogel nanoparticles, increased porosity of the plug and a higher insulin release rate.

Example 8

Biocompatibility of the Insulin Delivery Device

STZ (streptozotocin)-induced diabetic male Sprague Dawley rats were used for the in vivo experiments. To evaluate the biocompatibility of the device rats were randomized into 2 groups and implanted with silanized devices or PEGylated insulin delivery devices, both subcutaneously (SC) in the interscapular tissue and intraperitoneally (IP). After 5 days post-implantation, the animals were sacrificed and the devices were carefully explanted. Retrieved devices encapsulated with new-formed surrounding tissue were fixed in formalin 10%, embedded in paraffin and used for histological analysis.

The rats tolerated the devices very well as there were no signs of ongoing inflammation or insufficient wound healing at the sites of implantation. The biological response to the implanted devices was evaluated by histological analysis of the tissue surrounding the devices after 5 days implantation period. A significant difference between silanized and PEGylated devices was observed, either for IP or SC implantation. For the silanized device a very dense capsule is formed around the plug for devices implanted SC or IP. For the IP implantation a thick layer of inflammatory cells is observed in the device-tissue interface indicating an inflammatory reaction in response to the implanted device. A significant improvement in cellular response was found when PEG is introduced on the device surface. For devices with PEGylated surface a thin capsule or no capsule is observed for devices implanted SC or IP, respectively. The contrasting difference in encapsulation between PEGylated and silanized devices demonstrates a differential chronic tissue reaction in response to the surface chemistry of the device. These results indicate that the PEGylation of the device increases the biocompatibility by masking the device surface against immune cells response. Tissue encapsulation is dependent on the site of implantation and device surface chemistry.

Example 9

In vivo Performance of the Insulin Delivery Device

The performance of the insulin delivery device was evaluated in vivo by assessment of glycemia in diabetic-induced rats. Male Sprague-Dawley rats (300 g-350 g) were exposed to a 12/12 reverse-light cycle, fed rat chow and water ad libitum. Rats were induced to become diabetic by intraperitoneal injection of streptozotocin (STZ; 65 mg.kg$^{-1}$ in sterile saline). Before implantation surgery, rats were cannulated under isofluorane anesthesia to allow for easy daily blood samples. After three days of recovery, rats were randomized into 2 groups. Group 1 was implanted with saline-filled device (n=5, Sham) and group 2 was implanted with insulin-filled device (n=5, ~6 mg insulin implanted per rat). Fed glucose levels were monitored on a daily basis using a glucometer. Blood was withdrawn from the catheters for plasma insulin level determination using an antibody radioimmunoassay kit specific for rat insulin. After an 8-day implantation period, animals were sacrificed and the devices retrieved for further experiments.

Figure 9A:
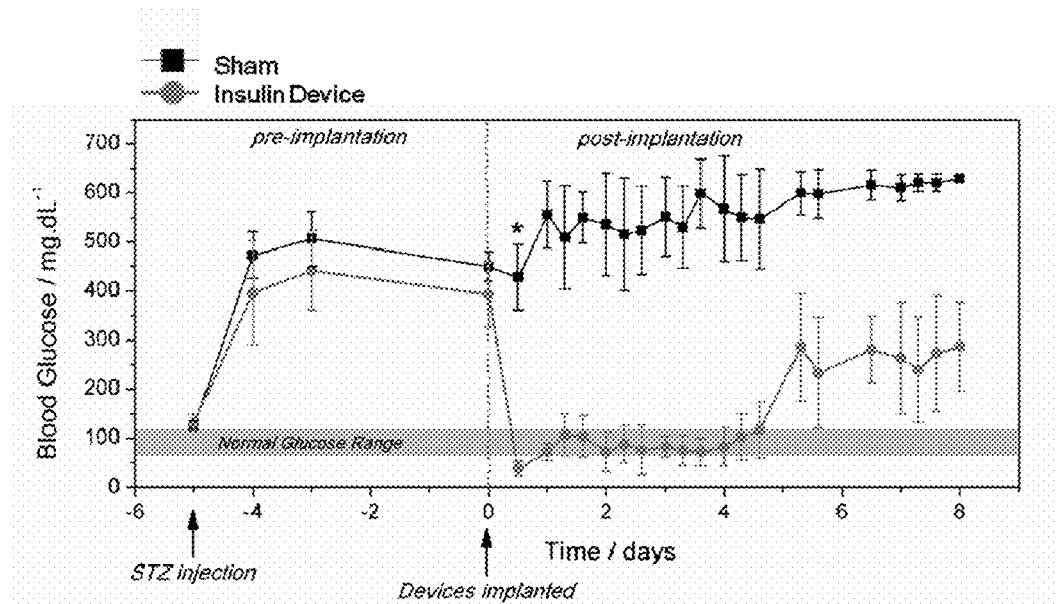
FIG. 9 graphically illustrates the effect of the device on the blood glucose levels (A) and insulin levels (B) in diabetic rats.
Figure 9B:
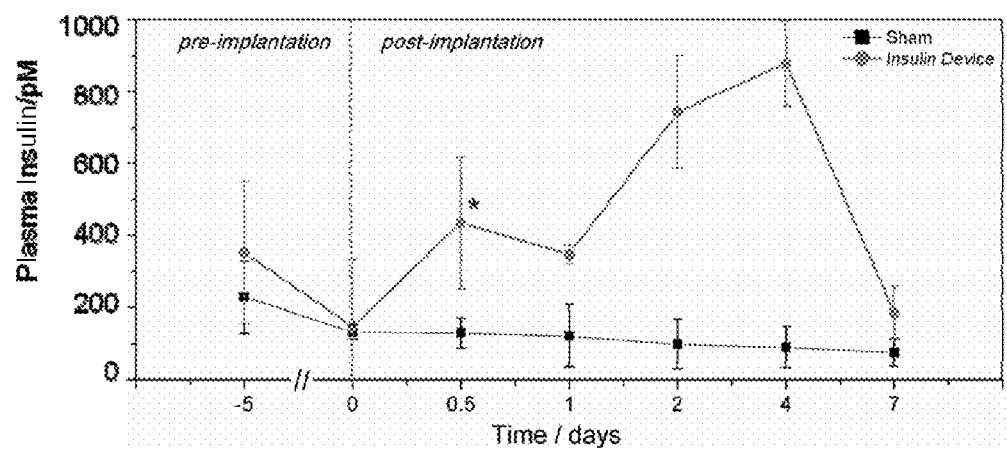

In the experiment, rats were induced to become diabetic by the injection of streptozotocin (STZ). STZ causes pancreatic β-cell destruction, resulting in a dramatic decrease in insulin levels. The diabetic state of the rats was confirmed with elevation in the blood glucose from 130 to >450 mg.dL$^{-1}$ (FIG. 9A). All rats were left untreated for 5 days to confirm the diabetic state prior to the intraperitoneal implantation of the device. The glucose levels and the plasma insulin levels of the rats were monitored on a daily basis during the 8-day implantation period. The device released insulin in vivo for up to 8 days. Rats implanted with insulin-filled device showed higher levels of plasma insulin than the sham group throughout the implantation period (FIG. 9B). The implantation of the insulin device caused a dramatic effect on the glycemic control of the diabetic rats compared to the sham. Upon implantation, animals in the insulin group showed an almost immediate drop of plasma glucose from hyperglycemic to hypoglycemic levels. However, this hypoglycemic effect seems to be mitigated over the course of the rest of the experiment and the blood glucose of the group was maintained in the normal level (~90 mg.dL$^{-1}$) for up to 6 days without peaks of hyper or hypoglycemic states (FIG. 9A). After 6-day implantation period, the blood glucose levels of the insulin group started increasing to hyperglycemic levels (~250 mg.dL$^{-1}$) but were still significantly lower than the sham (>600 mg.dL$^{-1}$). The increase in the blood glucose of the insulin group after 5-days implantation period was attributed to the decrease in the insulin content of the device (which could lead to lower insulin release rates) or due to loss of bioactivity of the encased insulin. It is also important to point out that, after 8-day implantation period, the group implanted with the insulin device gained weight and looked much healthier than the control group, evidencing the efficacy of the treatment with the insulin delivery device. A longer duration of effectiveness of the device containing higher insulin concentrations (i.e., 50 mg.mL$^{-1}$ and 100 mg.mL$^{-1}$ in a gel formulation) was obtained. Insulin release from the implanted device and suppression of glucose levels in diabetic rats lasted for 15 days.

Example 10

In vivo Glucose-Challenge Test of the Insulin Delivery Device

Figure 10:
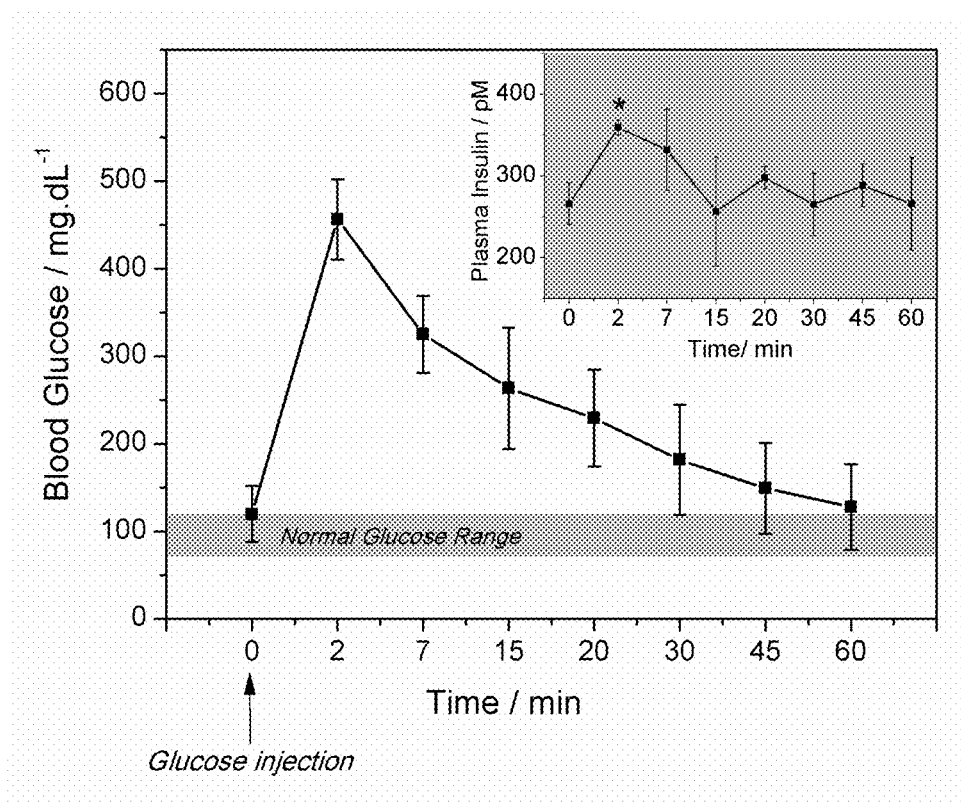
FIG. 10 is a graph showing the in vivo glucose-responsiveness of a device implanted in diabetic rats following a glucose challenge.

STZ-induced diabetic rats were implanted with insulin delivery device as described above and allowed for 24 h to confirm the decrease of blood glucose to normal levels by the action of the implanted devices. Rats were then challenged with intravenous injection of glucose (1 g.kg$^{-1}$, 50% dextrose), and their blood glucose was continuously monitored during 1 h. Upon the glucose injection the blood glucose level of the rat was increased from normal to hyperglycemic level; after less than 20 min the glucose was decreased to normal levels in response to the action of insulin delivered from the implanted device (FIG. 10). These results demonstrated the glucose-regulated profile of the device in vivo by challenging implanted rats with glucose.

We claim:
1. A biocompatible insulin delivery device comprising a reservoir for insulin and a glucose-responsive plug that seals the reservoir,
   wherein the plug comprises a polymeric matrix having an inorganic component and a stimulus-responsive component adapted to alter the porosity of the plug in response to a stimulus and wherein the plug functions to release insulin from the reservoir in response to a hyperglycemic glucose concentration and to prevent insulin release from the reservoir in response to a hypoglycemic glucose concentration.

2. The device of claim 1, wherein the reservoir is made of a biocompatible material selected from the group consisting of synthetic polymer, natural polymer, metal, glass, ceramic and hybrid materials formed with biocompatible metal, glass or ceramics with one or more polymers.

3. The device of claim 1, wherein the reservoir is made of a polymer selected from the group consisting of collagen, starch blends, hyaluronic acid, alginates, carrageenan, silicone rubbers, polydimethylsiloxane, polyurethanes, acrylic polymers, poly(methyl methacrylate), polyesters, cellulose derivatives, cellulose acetate, polyethylene terephthalate, polycarbonate, polysulfone, polyvinyl chloride, polyethylene, polypropylene, polymethylacrylate and nylon.

4. The device of claim 2, wherein the material is surface modified to include PEG or silane groups.

5. The device of claim 1, wherein the stimulius-responsive component comprises a composite of at least one hydrogel that changes porosity when exposed to a stimulus and at least one second polymer or polymer mixture that does not change when exposed to the stimulus.

6. The device of claim 5, wherein the hydrogel is selected from the group consisting of poly(ethylene oxide), polymers of R-acrylamide, R-acrylate or $R_1$-acrylic acid, and R, $R_1$, $R_2$-cellulose in which R, $R_1$, and $R_2$ may be H or alkyl.

7. The device of claim 5, wherein the second polymer is selected from the group consisting of crosslinked proteins and derivatives thereof, ethylcellulose, methylcellulose, propylcellulose, methoxypropylcellulose, hydroxypropylmethylcellulose, cellulose nitrate, poly(vinyl alcohol), poly(vinyl chloride), polystyrene, polyethylene, polypropylene, poly (ethylene-co-vinyl acetate), polyesters, poly(hydroxybutyric acid), poly(hydroxyvalerianic acid-co-hydroxybutyric acid), poly(lactic acid), poly(glycolic acid), poly(lactic acid-co-glycolic acid), poly(ε-caprolactones), poly(s-caprolactone-co-DL-lactic acid), polyanhydrides, poly(maleic anhydride), polyamides, albumin, gelatin, chitosan, collagen, pol(hydroxyalkyl)-L-glutamines, poly(γ-ethyl-L-glutaminate-co-glutamic acid), poly(L-leucine-co-L-aspartic acid), poly(proline-co-glutamic acid), poly(orthoesters), poly(alkyl2-cyanoacrylates), polylysin, alginate, alginic acid, polyurethanes, poly(methyl methacrylate), poly(methyl methacrylate-co-methacrylic acid) and poly(methacrylate-co-hydroxypropyl methacrylate).

8. The device of claim 5, wherein the stimulus-responsive component comprises a catalytic component that catalyzes the change in porosity in the hydrogel component in response to a change in the glucose level.

9. The device of claim 8, wherein the catalytic component comprises glucose oxidase.

10. The device of claim 9, wherein the catalytic component additionally comprises catalase.

11. The device of claim 1, wherein the inorganic component comprises inorganic particles selected from the group of particles suitable stabilize the polymeric matrix, particles suitable to quench hydrogen peroxide, particles suitable to regenerate oxygen and particles suitable to stabilize glucose oxidase.

12. The device of claim 11, wherein the inorganic component comprises one or more of $MnO_2$, Ag, Au, $SiO_2$, titanium, iron, magnesium, silica-based materials and carbon-based nanomaterials.

13. The device of claim 12, wherein the plug comprises inorganic particles in an amount in the range of about 0.01%-25% (w/w).

14. The device of claim 1, wherein the reservoir comprises an insulin formulation.

15. A method of treating diabetes in a mammal comprising implanting in the mammal a device as defined in claim 14.

16. The method of claim 15, wherein the device is implanted subcutaneously or intraperitoneally.

17. The device of claim 14, wherein the insulin formulation comprises hydroxypropyl methylcellulose.

\* \* \* \* \*